United States Patent
Ideta et al.

(10) Patent No.: US 11,771,068 B2
(45) Date of Patent: Oct. 3, 2023

(54) METHOD FOR PRODUCING NON-HUMAN LARGE MAMMAL OR FISH EACH CAPABLE OF PRODUCING GAMETE ORIGINATED FROM DIFFERENT INDIVIDUAL

(71) Applicant: National Federation of Agricultural Cooperative Associations, Tokyo (JP)

(72) Inventors: Atsushi Ideta, Kato-gun (JP); Masato Konishi, Kato-gun (JP); Yutaka Sendai, Tsukuba (JP); Shiro Yamashita, Tsukuba (JP); Ryosaku Yamaguchi, Sakura (JP); Marie Soma, Sakura (JP)

(73) Assignee: NATIONAL FEDERATION OF AGRICULTURAL COOPERATIVE ASSOCIATIONS, Tokyo (JP)

( * ) Notice: Subject to any disclaimer, the term of this patent is extended or adjusted under 35 U.S.C. 154(b) by 281 days.

(21) Appl. No.: 15/565,095

(22) PCT Filed: Apr. 6, 2016

(86) PCT No.: PCT/JP2016/061224
§ 371 (c)(1),
(2) Date: Oct. 6, 2017

(87) PCT Pub. No.: WO2016/163386
PCT Pub. Date: Oct. 13, 2016

(65) Prior Publication Data
US 2018/0116191 A1 May 3, 2018

(30) Foreign Application Priority Data
Apr. 8, 2015 (JP) .................................. 2015-078937

(51) Int. Cl.
*A01K 67/027* (2006.01)
*C12N 15/85* (2006.01)
*A61D 19/04* (2006.01)

(52) U.S. Cl.
CPC ........ *A01K 67/0276* (2013.01); *A01K 67/027* (2013.01); *A01K 67/0271* (2013.01); *C12N 15/8509* (2013.01); *A01K 2207/12* (2013.01); *A01K 2217/077* (2013.01); *A01K 2227/101* (2013.01); *A01K 2227/40* (2013.01); *A61D 19/04* (2013.01); *C12N 2510/00* (2013.01); *C12N 2517/04* (2013.01)

(58) Field of Classification Search
None
See application file for complete search history.

(56) References Cited

U.S. PATENT DOCUMENTS

| | | | | |
|---|---|---|---|---|
| 2004/0123337 A1* | 6/2004 | Gleicher | .............. | C12N 15/873 800/21 |
| 2005/0239040 A1* | 10/2005 | Lindenberg | .......... | C12N 5/0609 435/2 |
| 2011/0258715 A1 | 10/2011 | Nakauchi et al. | | |
| 2013/0211187 A1 | 8/2013 | Araki et al. | | |
| 2014/0359796 A1* | 12/2014 | Fahrenkrug | ........ | C12N 15/8509 800/15 |

FOREIGN PATENT DOCUMENTS

| | | |
|---|---|---|
| EP | 1 779 724 A1 | 5/2007 |
| EP | 2 258 166 A1 | 12/2010 |
| JP | 2014-121329 A | 7/2014 |
| JP | 5686357 B2 | 1/2015 |
| JP | 5688800 B2 | 2/2015 |
| WO | WO 02/10347 A2 | 2/2002 |

OTHER PUBLICATIONS

Tsuda et al, Conserved Role of Nanos Proteins in Germ Cell Development. Science, 2003. 301: 1239-1241.*
Mitalipov and Wolf. Totipotency, Pluripotency and Nuclear Reprogramming. 2009. In: Martin U. (eds) Engineering of Stem Cells. Advances in Biochemical Engineering / Biotechnology, vol. 114. Springer, Berlin, Heidelberg. pp. 185-199.*
Baguisi et al., "Production of goats by somatic cell nuclear transfer," Nature Biotechnol (May 1999), vol. 17, pp. 456-461.
Galli et al., "A cloned horse born to its dam twin," Nature (Aug. 7, 2003), vol. 424, p. 635.
International Search Report dated Jul. 12, 2016, in PCT International Application No. PCT/JP2016/061224.
Kato et al., "Eight Calves cloned from Somatic Cells of Single Adult," Science (Dec. 11, 1988), vol. 282, pp. 2095-2098.
Kobayashi et al., "Generation of Rat Pancreas in Mouse by Interspecific Blastocyst Injection of Pluripotent Stem Cells," Cell (Sep. 3, 2010), vol. 142, pp. 787-799.

(Continued)

*Primary Examiner* — Christopher M Babic
*Assistant Examiner* — Kimberly A Aron
(74) *Attorney, Agent, or Firm* — Birch, Stewart, Kolasch & Birch, LLP

(57) ABSTRACT

Disclosed is a novel means which makes it possible to steadily mass-produce knockout individuals even in large animals. The method of the present invention is a method for producing a non-human large mammal or fish (non-human animal) that produces gametes originating in a different individual, and comprises transplanting at least one pluripotent cell derived from a second non-human animal into an embryo derived from a first non-human animal, said embryo being at a cleavage stage and having a genome in which a function of nanos3 gene is inhibited, to prepare a chimeric embryo, and allowing said chimeric embryo to develop into an individual.

19 Claims, 5 Drawing Sheets

Specification includes a Sequence Listing.

(56) References Cited

OTHER PUBLICATIONS

Matsunari et al., "Blastocyst complementation generates exogenic pancreas in vivo in apancreatic cloned pigs," PNAS (Mar. 19, 2013), vol. 110, No. 12, pp. 4557-4562.
Onishi et al., "Pig Cloning by Microinjection of Fetal fibroblast Nuclei," Science (Aug. 18, 2000) vol. 289, pp. 1188-1190.
Tsuda et al., "Conserved role of nanos Proteins in Germ Cell Development," Science (Aug. 29, 2003), vol. 301, pp. 1239-1241.
Usui et al., "Generation of Kidney from Pluripotent Stem Cells via Blastocyst Complementation," Am. J. Pathol. (Jun. 2012), vol. 180, No. 6, pp. 2417-2426.
Wakayama et al., "Full-term development of mice from enucleated oocytes injected with cumulus cell nuclei," Nature (Jul. 23, 1998), vol. 394, pp. 369-374.
Wilmut et al., "Viable offspring derived from fetal and adult mammalian cells," Nature (Feb. 27, 1997), vol. 385, pp. 810-813.

\* cited by examiner

Vector for establishing a nanos3 (NOS3) heterozygous KO cell line

Genomic PCR analysis

NOS3 heterozygous KO cell lines (NOS3 –/wt)

①: P3-P2 (Within the vector)
②: P1-P2 (KO detection)

NOS3 heterozygous KO fetal cell line (line #3933: NOS3 –/wt)

SEQUENCE LISTING

<160> NUMBER OF SEQ ID NOS: 16

<210> SEQ ID NO 1
<211> LENGTH: 1171
<212> TYPE: DNA
<213> ORGANISM: Bos taurus
<220> FEATURE:
<221> NAME/KEY: CDS
<222> LOCATION: (385)..(903)

<400> SEQUENCE: 1
ctggttctcc tggaggagta gacaagggca gccctctcag tgccctctgg gtggggtgtg    60
tggctgctta ttgctggtac ccctgcagc ctgtgtcttg tcacgccccc tcacccttag   120
cctacccaga ggccatgcag ccccgtggca ggtgcatttc tgggggagc tgcagcaagc   180 ccctgtggc aatagggaac ctcctacagc ctgctcctcc ctcttcacac ccccttggag   240
tataaggagg gaactgacag cccagactcc tcggctccag agaggggaag ggaagggaga   300
ttaggcagaa gtagagagac cagcttgggg gcggctgcgt ttctcctgtc ttctgccct   360

| | | |
|---|---|---|
| ccacctggca cacggggccc agcc atg ggg acc ttc aac ctg tgg aca gac<br>                                    Met Gly Thr Phe Asn Leu Trp Thr Asp<br>                                      1               5 | 411 |
| tac ttg ggt ttg gca cgc ctg gtt ggg gct cag cgt gaa gaa gag<br>Tyr Leu Gly Leu Ala Arg Leu Val Gly Ala Gln Arg Glu Glu Glu<br>10                  15                 20                 25 | 459 |
| ccg gag acc agg ctg gat cgc cag cca gaa gca gtg ccc gaa ccg ggg<br>Pro Glu Thr Arg Leu Asp Arg Gln Pro Glu Ala Val Pro Glu Pro Gly<br>               30                 35                 40 | 507 |
| ggt cag cga ccc agc cct gaa tcc tca cca gct ccc gag cgc ctg tgt<br>Gly Gln Arg Pro Ser Pro Glu Ser Ser Pro Ala Pro Glu Arg Leu Cys<br>             45                 50                55 | 555 |
| tct ttc tgc aaa cac aac ggc gag tcc cgg gcc atc tac cag tcc cac<br>Ser Phe Cys Lys His Asn Gly Glu Ser Arg Ala Ile Tyr Gln Ser His<br>             60                 65                70 | 603 |
| gtg ctc aag gat gaa gcg ggc cgg gtg ctg tgc ccc atc ctc cgc gac<br>Val Leu Lys Asp Glu Ala Gly Arg Val Leu Cys Pro Ile Leu Arg Asp<br>75                  80                 85 | 651 |
| tac gtg tgc ccc cag tgc ggg gcc acc cgc gag cgc gcc cac acc cgc<br>Tyr Val Cys Pro Gln Cys Gly Ala Thr Arg Glu Arg Ala His Thr Arg<br>90                  95                100              105 | 699 |
| cgc ttc tgc ccg ctc acc ggc cag ggc tac acc tcc gtc tac agc tac<br>Arg Phe Cys Pro Leu Thr Gly Gln Gly Tyr Thr Ser Val Tyr Ser Tyr<br>             110                115              120 | 747 |
| acc acc cgg aac tcg gcc ggc aag aag ctg gtc cgc tcg gac aag gcg<br>Thr Thr Arg Asn Ser Ala Gly Lys Lys Leu Val Arg Ser Asp Lys Ala<br>             125                130              135 | 795 |
| agg acg cag gac cct gga cac gga ccg cgc cga gga gga ggt tcc aaa<br>Arg Thr Gln Asp Pro Gly His Gly Pro Arg Arg Gly Gly Ser Lys<br>          140                145              150 | 843 |
| ggt gcc agg aag tct tct gga act cct ccc tct tcc tgc tgc ccc tca<br>Gly Ala Arg Lys Ser Ser Gly Thr Pro Pro Ser Ser Cys Cys Pro Ser<br>155                 160                165 | 891 |
| act tct gcc taa ggagactggc gtgggcagga tgacgccttc acctggggat<br>Thr Ser Ala<br>170 | 943 |
| ggggacccag gctcagtgga ggctgggttt cagggaagac ccaccctccg aggatccgcc | 1003 |
| ccctagacgg tgcctccagc ctgggggctt ggcaaaggag cccggtctgg gaccaccgcc | 1063 |
| caaagcgcgc cgcccctgt cactgaaggg ggtggtcctc aggcacccct gcccttcttc | 1123 |
| cccaacgctg agcaaccagt cagcgctcaa taaatgttta tgaatgga | 1171 |

<210> SEQ ID NO 2
<211> LENGTH: 172
<212> TYPE: PRT
<213> ORGANISM: Bos taurus

<400> SEQUENCE: 2

Met Gly Thr Phe Asn Leu Trp Thr Asp Tyr Leu Gly Leu Ala Arg Leu
1               5                   10                 15

Val Gly Ala Gln Arg Glu Glu Glu Pro Glu Thr Arg Leu Asp Arg
          20                 25                30

Gln Pro Glu Ala Val Pro Glu Pro Gly Gly Gln Arg Pro Ser Pro Glu
        35                 40                45

Ser Ser Pro Ala Pro Glu Arg Leu Cys Ser Phe Cys Lys His Asn Gly
  50                55                60

Glu Ser Arg Ala Ile Tyr Gln Ser His Val Leu Lys Asp Glu Ala Gly
65               70                 75                80

```
Arg Val Leu Cys Pro Ile Leu Arg Asp Tyr Val Cys Pro Gln Cys Gly
                85                  90                  95

Ala Thr Arg Glu Arg Ala His Thr Arg Arg Phe Cys Pro Leu Thr Gly
            100                 105                 110

Gln Gly Tyr Thr Ser Val Tyr Ser Tyr Thr Thr Arg Asn Ser Ala Gly
        115                 120                 125

Lys Lys Leu Val Arg Ser Asp Lys Ala Arg Thr Gln Asp Pro Gly His
    130                 135                 140

Gly Pro Arg Arg Gly Gly Gly Ser Lys Gly Ala Arg Lys Ser Ser Gly
145                 150                 155                 160

Thr Pro Pro Ser Ser Cys Cys Pro Ser Thr Ser Ala
                165                 170

<210> SEQ ID NO 3
<211> LENGTH: 2200
<212> TYPE: DNA
<213> ORGANISM: Bos taurus

<400> SEQUENCE: 3
```

| | | | | | |
|---|---|---|---|---|---|
| ggaccgggtt | tgagggtgaa | gaaatgggga | agagcattaa | cggggtaagc | ctcgtgtagt | 60 |
| tatgcgcttg | ggccccgtc | tgatccgaca | agggcccgag | tttggaagcc | cgggacccct | 120 |
| tgcgatcctc | tagcttcgcc | cttgtccaac | cggcaggtgg | acccacaagg | cgggctaggc | 180 |
| agcggcccca | cctcggggct | cgaatttgca | aagtgcagac | tcagacaacc | ctcccccaa | 240 |
| ccaccttggg | ttgttgtgat | tcataaacca | ttgtgtccgg | aacacggtga | agctcactta | 300 |
| ggtattacat | tgtattaaaa | tgacttgttt | atctctccgt | tgcatccatg | ccccggggc | 360 |
| cagaaccact | tggcctccag | acctcttggg | gcctctcgga | atccctcctc | tgcctctgcc | 420 |
| tctagctaag | ggtgccctct | gttctggcct | gtctcccaaa | ctgataattg | gaagaaatat | 480 |
| gcaccgttga | gggcccttttt | gagaatgctt | tgactaaatg | ggttagaagc | ccagcgcccg | 540 |
| ctgctgctat | atttgcatag | caaaggtgac | agaagtatct | gctgatatta | ttacttagat | 600 |
| ttatctcctt | tttccctgtc | ctggagcaga | gttggctcct | tcctgctatc | tgttccctga | 660 |
| cttaatagat | tctctaagtc | tctcattccc | ttccctccc | tcaccctacc | cggttccttg | 720 |
| acccaccccg | cccccagcc | tccactccct | gcccccaag | gagttgccaa | gggtttgggg | 780 |
| gaacattcaa | cctgtcggtg | agtttgggca | gctcaggcaa | accatcgacc | gttgagtgga | 840 |
| ccccgaggcc | tggaactgcc | gtccacccac | ccacccatca | cgaccccaa | ctttcagatc | 900 |
| tggggcaggg | gcaggggatc | ccgaacacat | ccctcccctt | aggccacagc | gaaggtcaca | 960 |
| atcaacattc | attgttgtcg | gtgggttgtg | acagagacca | gacccaccga | gggatgaatg | 1020 |
| tcactgtggc | tgggccagac | acaatcctgg | actccccccc | tcccgccccc | caaaactgct | 1080 |
| cagccagaac | ctgaccctga | ccctggcctt | tcaccctcg | aggagggctg | gtgtctgggg | 1140 |
| tacttaaaga | cacaggctag | atttgggggc | atcaatcctg | gagggctgtg | acaggaatt | 1200 |
| acaagtttag | gactgggcag | ctgaaaaacc | tttctgaaag | ggattagggg | gccctgcttc | 1260 |
| cagaaggctc | agtgaagctt | tcttgaatga | atgaatgaat | gaggtgtgta | ggcggcacgt | 1320 |
| cacctcttct | ctgagttcca | gtcttgggcc | ctgctttctc | accttctta | cctggtacct | 1380 |
| gcagacccct | cctttacctt | cagttgccca | cctagcacct | gatgcccgtt | gatcacctgc | 1440 |
| cagtctgtgt | cccacctggg | tgactcgggg | gcacaccgca | tcctcctgag | atggagcgca | 1500 |
| ggtctcattt | gagagggcaa | tcaaggtcct | ggccaatcta | ggggtctccc | ctctgccccg | 1560 |
| ttagccccac | ctgtgcctgt | gctctcttcc | ccataatcct | cagtctcaaa | cccttttcca | 1620 |

-continued

```
cccccaggacc tggagagact gactccacaa cacctaaggc tcctgtaact ggtgggggag      1680
gcaggctttg ttgccttcgt gaataacccc agggcaggtg acttcaaacc cgtttgttca      1740
tcagctaaaa ggaggttcca ctgacaaggg gtgtgaaagc tccctgaggg tgaccagagg      1800
taggggcctt ggtccttgtc ccccccacc ataagacagg cccttcctcc ttccaaagtc       1860
agctggaagg tcagtggctc cccctccccc ctcccccagt cctggagaag gaagaaagaa      1920
gttactaagt tactgactac agcactgcta gtctttgggg tggggcttcc aatgccccca      1980
cctgcatcac tctggttctc ctggaggagt agacaagggc agccctctca gtgccctctg      2040
ggtggggtgt gtggctgctt attgctggta ccccctgcag cctgtgtctt gtcacgcccc      2100 ctcacccta gcctacccag aggccatgca gccccgtggc aggtgcattt ctgggggag        2160 ctgcagcaag cccctgtgg caatagggaa cctcctacag                             2200
```

<210> SEQ ID NO 4
<211> LENGTH: 7100
<212> TYPE: DNA
<213> ORGANISM: Bos taurus
<220> FEATURE:
<221> NAME/KEY: misc_feature
<222> LOCATION: (3758)..(3807)
<223> OTHER INFORMATION: unknown bases

<400> SEQUENCE: 4

```
gggcaggatg acgccttcac ctggggatgg ggacccaggc tcagtggagg ctgggtttca        60
gggaagaccc accctccgag gatccgcccc ctagacggtg cctccagcct gggggcttgg       120
caaaggagcc cggtctggga ccaccgccca aagcgcgccc gcccctgtca ctgaagggg        180 tggtcctcag gcaccctgc ccttcttccc caacgctgag caaccagtca gcgctcaata       240
aatgtttatg aatggatcag cgtcatacga agcccggtct tgggacaagg tatcgtgaac      300
tgcgccgctg gggctgtcgc gtccctcagc ctccatatgt tactctgatc tccggttcc      360 tcaactgcta tttggatttc ttttcgccct ggggcgctgg ggtgaggtgc tttgggctga      420
gaaatggcag ctgggggtc gccccagccc ggcacttctg agcagacatt tgcagtggag       480
ttagtgccat gaatcttgtt tctgtgactt ttgtgttgc agacttttct ggccacctct       540
tgcatattga catgtcagat gggtagatcc agcacactgg aggcggggc ctgatttgag       600 ggggcaatgg agaaacaatt agaggttccc ccatcgttgt cctcacctca gaagccctca    660
gtgaatgttt aggttaccat cgatgcccca gaaactgggg gccagagtca catgccaggc      720
ccttcagaac aagggaagga cttctgggtt ggggcagggt gagggttggg ggccataagg      780
aatgggaata tgtcctggtc agttgtgcca gacaacagct gggcaaggg gcactgtgga      840 ggctgtactt cttcaggagt gggaggggac agaggtccat ccccaccctg gtagtgtgat     900
ctggttctcc tgggggcttt ggcttggggg gatccccacc ccatgtctcc accccagat      960 cttgttccac cagccttgag ggggcagcag gtaagaagtg ccagtccaca ttccttctcc     1020
agtccgaggg ctggcctgag cctggtctcc acccccagcc tacaaggtct cctggggttg     1080
agtcagggca gaatttgggc ttcccagaat ttgcccttgg cttttgccatt tgatctggga    1140 cctgaggcca cctgaggagg gctgcggtga gccaggatc agaaacggcc cttgaagaca       1200
gcctactgcc caggcttgga gagaaaggg aaggaggaga aagaagacat gagggaggcc      1260
tcctcagcag tgccaagggt ttcacatgga gtcagggac acagtacccc agccactctc      1320
agctacgtac aaatgctaat tatataagcc agagccactg gggcttgaga cccagggaac    1380
```

```
agggtgactg ggcacattct ggtgggttca aggaaggggc tgtacattct gcagggtaaa    1440
aaggctgggg gactctgagc cacctgaatg ggatgtccca ggtataagaa ggtggtggca    1500
ggagggccct ccctgccttg gccctaggag ttagggtgca ggggcgacag gcagagcaac    1560
aaattagtct tgggtctggt ccacctagtg gtgacctatt taacagaagc aatgtcttct    1620
gcaaaacggg tttgacagca gcacttggga ctgctagtga ccatgtgacc tcactggggc    1680
tgtggtgagg cttggtgggg cagggtgtgc gcacgcttgc cctcggcacc ctccaggcat    1740
tagctgtgtc tgcatcagtt ataattccca cccaggggttg cctcctagac cagggcttct    1800
cagcagcttg tcccacagag gagaggcaag gccaactcag cactgaactc cagcttggac    1860
agtcaagatg tctcagtggg ctgattggtc cacagatact tgtgtgctgg aatttgtaca    1920
catgcacatc tctgcacata cccacctgct ccaggagagt ctgacacttg ctaaagcatg    1980
gggaccccta gactccatct gggagtgggg gccccggca gtacaccaac ttgtcttcac    2040
aaagagcatg agaaacagaa ggagaacaag gtggtattag ggaggtttgt gggcaggcca    2100
tcaaggaact gaaaacacct ccaaccgcaa acaggtcggt cacacggtct gaggtctggc    2160
taaggcatca tttattaatg ggcttcccag aagaaatgga aatccagtga aaaacaaggg    2220
tatgaccaac aaagcaagcc cttttctcct ccaggaaaga aacaaattct gaaccttcag    2280
taacctcagc taaggagctg aaatttgcaa actcagataa ccatctgggt ggccccgcgc    2340
ccctggctca gaagcagctg gcttcctggg gccccagaag gcctgccaca gggaggagca    2400
ggttccccgc cccacgcagc tcccagggga ggccgatgac agaggcaggg cctctcgtgt    2460
ttcccgtggg aagctgactt ccccgtcagt tgagggacgg tttctggggc ccccaggacc    2520
ggcacgtgag aaggtcaaga tagcagggtg gggggagcga gcacacaggg tctgcagagg    2580
gattgttccc cactgttggg caggacattt ctgggagcca gtgagcttgc aggaacacac    2640
accacaaccc caggcagttt ggaaccagct acagatccct ccaggactgc tcccctcggg    2700
ggagggttcc tgccccctttt gcggtgtagg gtgtggggggc cttcccggcc ggcttttgctt    2760 tccggtagta gttgaggcgc ttgaaggtct ccaggtcccg gtgggtgctc ataatcagcc    2820
ggctgggtga aaacaggcct gggctgtgcc ccacctcaca ctcgggcaca ctgggctgct    2880
cacatcggct cactcgctca tgggtactcg ggtcacaccc gcataagcac aggcgtgtgc    2940
acagtccgca tcagcctgct gcaggcaggc tgtgacccctt ctagcccctc cttagagcct    3000
gacaactctg tgaaggagaa gcttcccaga ggcccctcac ggggggggggc tgggcccagc    3060 ctggctcccc cagatcactg gtacactggg gcctccatca cccaccccccg gctccattcc    3120 ctctgcctgt cccagggact gtgggtccac ggtgccagcc cagcccttac ttcaggttgg    3180
agagctccat gaccaggccc ctcacggtgt ccgtcgcgtc ctctatgctg gcggcctcgt    3240
aagtcttgat ccccactcgt gtcctggcgg gaagggaggc aggaggagag ctcactggag    3300
agccccacca gcctccactg ggggcgctct gctgagcctt gagccatctc tccagagatg    3360
aacacctttg acagccatga cgccccctcc caccaggcag ggtcctgatg gccagcccca    3420
tggctctacc gcttaaaata cacccagaat ctagccccctt cccccaccag gtggctcctg    3480
tggggcagtt gccacaccct cctcggcccc cacctcctgc ccttatatcc tgtcccctca    3540
agtggcttgg tgggggggggc tgtggaaatg gaaacccagc ccaaatctct ccccgcagcc    3600
ctacaccatc cgccgtgcct ccagaccccac ccactccctc ttgtccctct tccccctgtt    3660
gcagccacac tgaattcctg gccattcccg tagcacttct tagggctctg aaatgttctt    3720
tccagaatgt ctcctccgtg ggggtggggg aggagannnn nnnnnnnnnn nnnnnnnnnn    3780
```

```
nnnnnnnnnn nnnnnnnnnn nnnnnntcc ccatccaccc acaggttaaa atcttaaccc      3840
cttccctgct atcttttct ccccaccact ctgccatctg accagctaat aatttgtctg       3900
ttgctcacca ccaccccca agctcccacc caactaggga gaagctgtgt tctccccag        3960
tgcccagagc aggtcctgga agacctggca ttggagggca tcagtgccta tagaaggggt      4020
agacaggcgg ggcaccactg tatctaatag gtatagcctg tggggaggga gcagagggtc      4080
atacagctta gcagattcct gggctgtcac tagaggaact gtggttctgc tcccctgct       4140
ttagtcaccc tgagatgact ggtcagcctg ggcctcagtt tcttgccttt tctctcttgg      4200
ccaagggcca tagaagcaga ccccaggacc cacctggggg cttccagcca tccacgtggg      4260
gttgcattga ggccgtcaag agattcacac gccaatctcc ctccttttg cttaagcaat       4320
agtaggggcc ttctctggtg gttcagaggc taagagtccg cctgccagtg caggggacat      4380
gggtttgatc cctggtctgg gaagattcga catgctgcgg agccactaag cccatgcttt      4440
agagcctatg ctctgcagtc agagaagccg ccacagtgag aagcctgtgc actgcaacaa      4500
agaggagccc gtgctctctg caactggaga aaatctgtga gcagcaacaa ggacccagca      4560
caacaaaaat aaatgttaaa aaaaacaaca gtggggccac gttgattaaa ctgcctctgg      4620
tccccaggca gggagcgggt gtgtgtgtct gtcagggaa gcaacatgtg gtaccacagg       4680
tactatacac agatgtgtgc aagggcaggg ggtgggaggc cccctcttc cctgaggagg       4740
aggagcagga ggaagagaaa ggagacaaat tccgccaagg gttgcatgcc tcatctctcc     4800
tccacacctg ccagagagaa acagaaactt ggccataaat aatcaatcgg ccaccgctct      4860
gcagtttaag tacaaggtaa caggagagga ctgtcgccct gtgctggtgg tcagcaaggc     4920
tgggagaaag gacatgaaca gaggtgatgg actgggagag ggaagctctg gggtgggggg      4980
agaggaccct cccaacacac acctccatgg gctggaggag cacccgggt gcctatagga       5040
gggagagaag gtggctgcct tggggaacag aaccaagcag gaaagaagac gggacagact      5100
ggggactctg gaaggcccga gggtgccaga gcaggggtgg ccccgaggtc acgcaggcca     5160
gtggctccga gctctgactg ggtccctact ccctccatgg agattcaagg aaagctctgg     5220
gctgtctctc caataaaacg cacaacatgc attcaaacca ccacagagct gggggcacca     5280
tcccaaggga cctagggaga gatgccagct tgggtgcagg gtgctgactg ggagttctcc     5340
actcccaggg agcaggggc atgggaagtt tgcaagtggg agtgggaacc ttcctggtgg      5400
tccagtgatt aagactgcat tgcaacgcag gggacctggt ttcaaaccct ggtggggact     5460
aggatcccat gccaagtggc atggccgaaa agcgaaaatg aaaaaatctg gggacttccc     5520
tagtggccca atggttaaga ctctgtgctc ccagtgcagg gggcctggat ttgatccctg     5580
ctcagggaac tagatccagc atgttgcaac tacaaccccg cgcagccaca taagtaagaa     5640
attcagggct tagcaaccct attagacaga gaaagtgag gccctcgag ggagagccag       5700
ggtcacctcc atcaccctca ttcacaaagt gggagctcaa aaggcagggg tggggggag      5760
gtggggggctg gagccccagc aaagcagcca cgctccccct tcgagagaca agaggaggac    5820
tccggccaag gcaaggtccc acggtgcctc ccactctgcc tacctcggct gggcctcagc    5880
acggggggcct ctgtctgcac acgggccggt gccaggctgg caggggtcca gctcgcctcc   5940
tgcaggaaac aactggaaaa ggagagtgcg cacacatgtg agtgacccgg ctgggagaag    6000
gagaggagcc acgcaggtct ggcttctcct ccaccacact cggaaggctg aggcgtgctt     6060
tcctcctgca gaggaggaaa agtggtgtgg gggacagatg ccgtgacagc cagacctgca    6120
```

```
ggccaccagt ccggctgctc tcaccctccc tcctcgatac taggcctgac cctggcgtcc      6180
tctcctgggc cccagtcttc ggacaagctg atctgagcca ccgcggggtg gttccatccc      6240
atattctctg tccctgaccc ctgaggcctg gtgtggtctc aggcctgtcc tgcggtatct      6300
aggaggggtc agagaggacc ccgggggtgc tgactgtggt gaggcgggcg gctggcatgg      6360
aggggcagag tcggccagat aagccccgag tttcatgtca aggaaaagat tttgcaaata      6420
tattttgaag ggaacattca taattaacgg gggcgagaga gccagataac cctgagaagc      6480
ttaaatttct aaaggtcaac ggtggtttaa ttttcatgga aaatgtcagg ctcagtggct      6540
cagtggcgca ggtgacggct cttttgcctct ttggagccgc tggcccaggg ctgtctgttc      6600
ttctgaggag acacaagtcc taggtggggg atgccgtgaa gggtttgagc acaacctgcc      6660
aagggtcctg ggatacaaag gaatggacat gaagaactgt ctgcagtcca gcagctttca      6720
ctcagggatg actccagccc caagacacat catagtgtct gcaaacattt tgggttgtca      6780
cgcctttgca agaaggtgct cctcgtgttc agagggtggg ggctggaggc cagggatgct      6840
gttcaacccc cttccatgta caggatggcg gccaggcccc caacgccagc agtgccaagg      6900
ttggcacgac tgttctaggc agtggtttct cccatgcaca cagccgactc tcacggaggc      6960
aactctgtga cttaaagtac aattcaggga cttccctcgt ggtccagagg ttaagactct      7020
tcgctcccaa tgcagggggt cccgggtccg atccctgatc agggaactag attctgcatg      7080
gcgcaactaa gacccagcac                                                  7100

<210> SEQ ID NO 5
<211> LENGTH: 3050
<212> TYPE: DNA
<213> ORGANISM: Artificial Sequence
<220> FEATURE:
<223> OTHER INFORMATION: pNOS3-huKO-KIb, short arm

<400> SEQUENCE: 5
gtcgactctc cgttgcatcc atgccccgg  ggccagaacc acttggcctc cagacctctt        60
ggggcctctc ggaatccctc tctgcctct gcctctagct aagggtgccc tctgttctgg       120
cctgtctccc aaactgataa ttggaagaaa tatgcaccgt tgagggccct tttgagaatg       180 cttttgactaa atgggttaga agcccagcgc ccgctgctgc tatatttgca tagcaaaggt       240
gacagaagta tctgctgata ttattactta gatttatctc cttttttccct gtcctggagc       300 agagttggct ccttcctgct atctgttccc tgacttaata gattctctaa gtctctcatt       360 ccccttcccct ccctcaccct acccggttcc ttgaccacc ccgcccccca gcctccactc       420
cctgcccccc aaggagttgc caagggtttg ggggaacatt caacctgtcg gtgagtttgg       480
gcagctcagg caaaccatcg accgttgagt ggaccccgag gcctggaact gccgtccacc       540
cacccaccca tcacgacccc caactttcag atctggggca ggggcagggg atcccgaaca       600 catccccctcc cttaggccac agcgaaggtc acaatcaaca ttcattgttg tcggtgggtt       660
gtgacagaga ccagacccac cgagggatga atgtcactgt ggctgggcca gacacaatcc       720
tggactcccc ccctcccgcc ccccaaaact gctcagccag aacctgaccc tgaccctggc       780
cttcaccccg tcgaggaggg ctggtgtctg gggtacttaa agacacaggc tagatttggg       840
ggcatcaatc ctggagggct gtggacagga attacaagtt taggactggg cagctgaaaa       900
acctttctga aagggattag ggggccctgc ttccagaagg ctcagtgaag ctttcttgaa       960
tgaatgaatg aatgaggtgt gtaggcggca cgtcacctct tctctgagtt ccagtcttgg      1020
gccctgcttt ctcacccttc ttacctggta cctgcagacc cctcctttac cttcagttgc      1080
```

-continued

```
ccacctagca cctgatgccc gttgatcacc tgccagtctg tgtcccacct gggtgactcg    1140
ggggcacacc gcatcctcct gagatggagc gcaggtctca tttgagaggg caatcaaggt    1200
cctggccaat ctaggggtct cccctctgcc ccgttagccc cacctgtgcc tgtgctctct    1260
tccccataat cctcagtctc aaacccttt ccaccccagg acctggagag actgactcca     1320
caacacctaa ggctcctgta actggtgggg gaggcaggct tgttgccctt cgtgaataac    1380
cccagggcag gtgacttcaa acccgtttgt tcatcagcta aaaggaggtt ccactgacaa    1440
ggggtgtgaa agctccctga gggtgaccag aggtaggggc cttggtcctt gtccccccc    1500 accataagac aggcccttcc tccttccaaa gtcagctgga aggtcagtgg ctcccctcc    1560 cccctccccc agtcctggag aaggaagaaa aagttactaa agttactgac tacagcactg   1620
ctagtctttg gggtggggct tccaatgccc ccacctgcat cactctggtt ctcctggagg    1680
agtagacaag ggcagccctc tcagtgccct ctgggtgggg tgtgtggctg cttattgctg    1740
gtaccccctg cagcctgtgt cttgtcacgc cccctcaccc ttagcctacc cagaggccat    1800
gcagccccgt ggcaggtgca tttctggggg gagctgcagc aagccccctg tggcaatagg    1860
gaacctccta cagcctgctc ctccctcttc acaccccctt ggagtataag gagggaactg    1920
acagcccaga ctcctcggct ccagagaggg gaagggaagg gagattaggc agaagtagag    1980
agaccagctt gggggcggct gcgtttctcc tgtcttctgc ccctccacct ggcacacggg    2040
gcccagccat gggctcgacg atcaagcccg agatgaagat gaagtacttc atggacggca    2100
gcgtgaacgg ccacgagttc accgtggagg cgagggcac cggcaagccc tacgagggcc     2160
accaggagat gaccctgagg gtgacaatgg ccaagggcgg ccccatgccc ttcagcttcg    2220
acctggtgag ccacaccttc tgctacggcc acaggccctt caccaagtac cccgaggaga    2280
tccccgacta cttcaagcag gccttccccg agggcctgag ctgggagagg agcctccagt    2340
tcgaggacgg cggcttcgcc gccgtgagcg cccacatcag cctgaggggc aactgcttcg    2400
agcacaagag caagttcgtg ggcgtgaact tccccgccga cggccccgtg atgcagaacc    2460
agagcagcga ctgggagccc agcaccgaga agatcaccac ctgcgacggc gtgctgaagg    2520
gcgacgtgac catgttcctg aagctggccg gcggcggcaa ccacaagtgc cagttcaaga    2580
ccacctacaa ggccgccaag aagatcctga agatgccccc gagccacttc atcggccaca    2640
ggctggtgag gaagaccgag gcaacatca ccgagctggt ggaggacgcc gtggcccact      2700
gctgaattgc ttctgcctaa ggagactggc gtgggcagga tgacgccttc acctggggat    2760
ggggacccag gctcagtgga ggctgggttt cagggaagac ccaccctccg aggatccgcc    2820
ccctagacgg tgcctccagc ctgggggctt ggcaaaggag cccggtctgg gaccaccgcc    2880
caaagcgcgc ccgccctgt cactgaaggg ggtggtcctc aggcacccct gcccttcttc     2940
cccaacgctg agcaaccagt cagcgctcaa taaatgttta tgaatggatc agcgtcatac    3000
gaagcccggt cttgggacaa ggtatcgtga actgcgttaa gggcgaattc                3050
```

<210> SEQ ID NO 6  
<211> LENGTH: 20  
<212> TYPE: DNA  
<213> ORGANISM: Artificial Sequence  
<220> FEATURE:  
<223> OTHER INFORMATION: sense primer for amplification of nanos3 KO  
   1.5 kb short arm

<400> SEQUENCE: 6

```
ctctccgttg catccatgcc                                                   20
```

<210> SEQ ID NO 7
<211> LENGTH: 22
<212> TYPE: DNA
<213> ORGANISM: Artificial Sequence
<220> FEATURE:
<223> OTHER INFORMATION: antisense primer for amplification of nanos3
      KO 1.5 kb short arm

<400> SEQUENCE: 7
agccactgac cttccagctg ac                                              22

<210> SEQ ID NO 8
<211> LENGTH: 21
<212> TYPE: DNA
<213> ORGANISM: Artificial Sequence
<220> FEATURE:
<223> OTHER INFORMATION: sense primer for amplification of nanos3 KO
      6.5 kb long arm

<400> SEQUENCE: 8
ggacaaggta tcgtgaactg c                                               21

<210> SEQ ID NO 9
<211> LENGTH: 22
<212> TYPE: DNA
<213> ORGANISM: Artificial Sequence
<220> FEATURE:
<223> OTHER INFORMATION: antisense primer for amplification of nanos3
      KO 6.5 kb long arm

<400> SEQUENCE: 9
aacacgagga gcaccttctt gc                                              22

<210> SEQ ID NO 10
<211> LENGTH: 22
<212> TYPE: DNA
<213> ORGANISM: Artificial Sequence
<220> FEATURE:
<223> OTHER INFORMATION: primer P1

<400> SEQUENCE: 10
aacacggtga agctcactta gg                                              22

<210> SEQ ID NO 11
<211> LENGTH: 20
<212> TYPE: DNA
<213> ORGANISM: Artificial Sequence
<220> FEATURE:
<223> OTHER INFORMATION: primer P2

<400> SEQUENCE: 11
catgctccag actgccttgg                                                 20

<210> SEQ ID NO 12
<211> LENGTH: 20
<212> TYPE: DNA
<213> ORGANISM: Artificial Sequence
<220> FEATURE:
<223> OTHER INFORMATION: primer P3

<400> SEQUENCE: 12
ctctccgttg catccatgcc                                                 20

<210> SEQ ID NO 13
<211> LENGTH: 23

```
<212> TYPE: DNA
<213> ORGANISM: Artificial Sequence
<220> FEATURE:
<223> OTHER INFORMATION: primer P4

<400> SEQUENCE: 13
cttcatctcg ggcttgatcg tcg                                            23

<210> SEQ ID NO 14
<211> LENGTH: 21
<212> TYPE: DNA
<213> ORGANISM: Artificial Sequence
<220> FEATURE:
<223> OTHER INFORMATION: primer P5

<400> SEQUENCE: 14
gcttcatcct tgagcacgtg g                                              21

<210> SEQ ID NO 15
<211> LENGTH: 21
<212> TYPE: DNA
<213> ORGANISM: Artificial Sequence
<220> FEATURE:
<223> OTHER INFORMATION: primer P6

<400> SEQUENCE: 15
ccacgtgctc aaggatgaag c                                              21

<210> SEQ ID NO 16
<211> LENGTH: 24
<212> TYPE: DNA
<213> ORGANISM: Artificial Sequence
<220> FEATURE:
<223> OTHER INFORMATION: primer P7

<400> SEQUENCE: 16
ctgatacgta agcctagcta ctcg                                           24
```

METHOD FOR PRODUCING NON-HUMAN LARGE MAMMAL OR FISH EACH CAPABLE OF PRODUCING GAMETE ORIGINATED FROM DIFFERENT INDIVIDUAL

TECHNICAL FIELD

The present invention relates to a method for producing a non-human large mammal or fish that produces gametes originating in a different individual.

BACKGROUND ART

In order to analyze gene functions in an organism precisely, it is essential to mass-produce organisms in which a gene of interest is knocked out (KO). Gene KO mice are important model organisms. KO mice are, in general, made relatively easily by injecting embryonic stem cells (hereinafter referred to as ES cells) that have undergone homologous recombination into blastocysts.

However, when KO animals are produced by using cattle, pigs, and the like whose ES cells have not established, a somatic cell nuclear transfer (SCNT) technique is required. Although studies have thus far been conducted on production of many kinds of SCNT animals including sheep, mice, cattle, goats, pigs, and horses (Non-Patent Documents 1 to 5), yet steady mass-production of KO large animals is, as it stands, extremely difficult due to frequent occurrence of low fertility, spontaneous abortion, stillbirth, death immediately after birth, and the like.

PRIOR ART DOCUMENT(S)

Patent Document(s)

Patent Document 1: JP 5686357 B
Patent Document 2: JP 5688800 B
Patent Document 3: JP 2014-121329 A

Non-Patent Document(s)

Non-Patent Document 1: Wilmut, I. et al. Viable offspring derived from fetal and adult mammalian cells. Nature 385, 810-813 (1997).
Non-Patent Document 2: Wakayama, T. et al. Full-term development of mice from enucleated oocytes injected with cumulus cell nuclei. Nature 394, 369-374 (1999).
Non-Patent Document 3: Kato, Y. et al. Eight calves cloned from somatic cells of a single adult. Science 282, 2095-2098 (1998).
Non-Patent Document 4: Baguisi, A. et al. Y. Production of goats by somatic cell nuclear transfer. Nature Biotechnol 17, 456-461 (1999).
Non-Patent Document 5: Onishi, A. et al. Pig cloned by microinjection of fetal fibroblast nuclei. Science 289, 1188-1190 (2000).
Non-Patent Document 6: Galli, C. et al. A cloned horse born to its dam twin. Nature 424, 635 (2003).
Non-Patent Document 7: Kobayashi, T. et al. Generation of rat pancreas in mouse by interspecific blastocyst injection of pluripotent stem cells. Cell 142, 787-799 (2010).
Non-Patent Document 8: Usui, J. et al. Generation of kidney from pluripotent stem cells via blastocyst complementation. Am. J. Pathol 180, 2417-2426 (2012).
Non-Patent Document 9: Matsunari, H. et al. Blastocyst complementation generates exogenic pancreas in vivo in apancreatic cloned pigs. Proc Natl Acad. Sci. USA 110, 4557-4562 (2013).
Non-Patent Document 10: Tsuda, M. et al. Conserved role of nanos proteins in germ cell development. Science 301, 1239-1241 (2003).

SUMMARY OF THE INVENTION

Problems to be Solved by the Invention

An object of the present invention is to provide a novel means which makes it possible to steadily mass-produce knockout individuals even in large animals.

Means for Solving the Problems

It has been shown that when an early embryo in which a particular gene is knocked out is mixed with a normal early embryo to prepare a hybrid embryo (chimeric embryo) which is then allowed to develop, a deficient part of a cell derived from KO embryo is compensated by a cell derived from the normal embryo in the hybrid embryo (Non-Patent Documents 6 to 9 and Patent Documents 1 to 3). This technique is known as a blastocyst complementation technique. Meanwhile, nanos3 gene is a gene associated with germ cell differentiation that is specifically expressed in primordial germ cells, and it has been reported that knockout of nanos3 in mice results in no formation of germ cells (sperm and eggs) (Non-Patent Document 10).

The present inventors have paid their attention to these techniques and discovered that when a chimeric embryo is produced using a nonos3-KO/SCNT embryo as a host embryo and a cell derived from a particular gene-KO/SCNT embryo as a donor cell, sperm and eggs of the thus-produced individual may all be in the state where the particular gene is knocked out, and particular gene-KO large animals are likely to be steadily obtained by subjecting the female and male of the animal produced as describe above to crossing (artificial insemination or in vitro/external fertilization). The inventors have intensively studied using cattle as a representative example of large animals to confirm that germ cells are lost upon nanos3 gene KO in the Japanese Black, and further successfully complemented Holstein germ cells by injecting blastomeres of Holstein's fertilized egg to a nanos3-KO/SCNT embryo of the Japanese Black, thereby completing the instant invention.

That is, the present invention provides a method for producing a non-human large mammal or fish that produces gametes originating in a different individual, said method comprising transplanting at least one pluripotent cell derived from a second non-human large mammal or fish into an embryo derived from a first non-human large mammal or fish, said embryo being at a cleavage stage and having a genome in which a function of nanos3 gene is inhibited, to prepare a chimeric embryo, and allowing said chimeric embryo to develop into an individual. The present invention also provides a method for producing an egg of a non-human large mammal or fish, said method comprising collecting an egg from a female individual of said non-human large mammal or fish produced by the above-described method according to the present invention. The present invention further provides a method for producing sperm of a non-human large mammal or fish, said method comprising collecting sperm from a male individual of said non-human large mammal or fish produced by the above-described method according to the present invention. The present invention still further provides a method for producing a fertilized egg of a non-human large mammal or fish, said method comprising fertilizing an egg with sperm, both of which are produced by the above-described methods according to the present invention, to obtain a fertilized egg. The present invention still further provides a method for producing a non-human large mammal or fish, said method comprising obtaining a descendant of female and male non-human large animals or fish produced by the above-described method according to the present invention by natural mating, artificial insemination, or in vitro fertilization.

Effect of the Invention

According to the present invention, it is possible to steadily supply individuals in which a desired particular gene is knocked out even in large animals although it has conventionally been found to be very difficult to steadily mass-produce knockout individuals in such large animals. Steady mass production of knockout individuals is one of the aspects of the present invention; and according to the present invention, it also becomes possible to steadily supply non-human animals having desired genetic characteristics besides knockout animals at a low cost. Examples of specific applications of the present invention include the following applications.

(1) Establishment of KO Large Animal Strain

A pluripotent cell (ES-like cell, blastomere, and the like) derived from an individual in which a desired gene (gene A) is knocked out is injected into a nanos3-KO cell nuclear transfer embryo to complement germ cells, and the resultant is allowed to develop into an individual. Gene A-KO sperm and gene A-KO eggs can be steadily obtained from male and female, respectively. A gene A-KO individual can be steadily mass-produced by mating (natural mating, artificial insemination, or in vitro fertilization) the male and the female.

(2) Mass Production of Eggs of an Individual Having Desirable Characteristics without Resorting to Cloning Techniques A pluripotent cell (ES-like cell, blastomere, and the like) derived from an individual having desirable genetic characteristics is injected into a nanos3-KO cell nuclear transfer embryo to complement germ cells, and the resultant is allowed to develop into an individual. Such an individual produces sperm or eggs having the desirable genetic characteristics. If the individual is produced using a phyletic line with high ovulation number (that is, such a phyletic line may preferably be used as a nanos3-KO cell line and a nuclear transfer recipient), sperm, eggs, and fertilized eggs having the desirable genetic characteristics can be mass-produced at low cost.

(3) Allowing Animals that can be Raised at Low Management Costs to Produce Sperm and Eggs from Different Species and Producing Fertilized Eggs Inexpensively A pluripotent cell derived from the Japanese Black which has excellent gain ability is injected into a nanos3-KO/nuclear transfer embryo of goats or sheep to complement germ cells, and the resultant is allowed to develop into an individual (goat, sheep). The individual (goat, sheep) produces sperm or eggs of the Japanese Black which has excellent gain ability. A large number of fertilized eggs of the Japanese Black can be produced from the goat and sheep that can be raised at low management costs. This is practicable not only in mammals but also in marine organisms. For example, horse mackerel or mackerel that produces sperm and eggs of tuna can be obtained by preparing a nanos3-KO/nuclear transfer embryo using horse mackerel or mackerel, and complementing germ cells of tuna. Tuna can be obtained by raising those horse mackerel and mackerel.

(4) Establishment of Y Sperm-Inactivated Cattle (Cattle Lineage Bearing Only Female)

SRY gene is a gene on Y chromosome that functions to allow the gonad rudiment to differentiate into the testis. Inactivation of the SRY gene results in female births even when Y sperm fertilizes. In prior art, sperm selection by using a flow cytometer is required when female births are preferred. However, the vitality of sperm is decreased due to this selection procedure. By complementing germ cells of a nanos3-KO embryo using a nuclear transfer embryo in which SRY is knocked out as a donor in accordance with the present invention, a lineage of large animal that gives birth to only female due to inactivation of Y sperm can be created.

MODE FOR CARRYING OUT THE INVENTION

Figure 1:
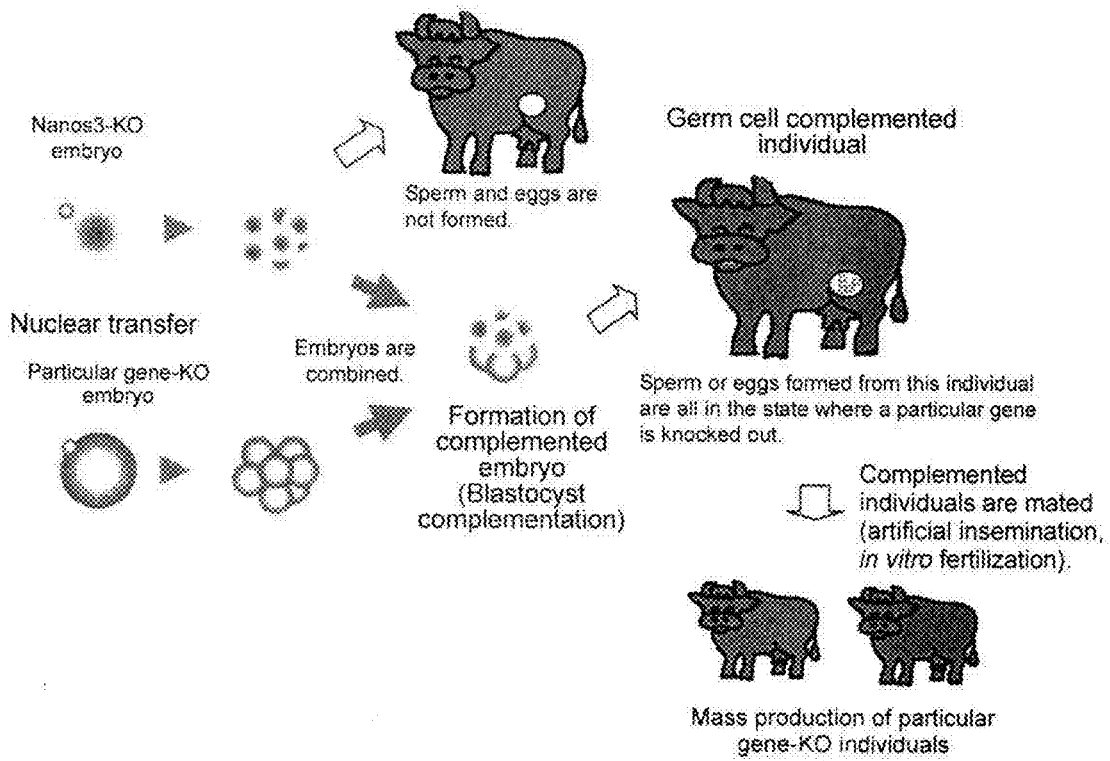
FIG. 1 shows the outline of the technique of the present invention.

Animals subjected to the present invention are non-human large mammals or fish. Hereinafter in the present specification, non-human large mammals and fish may both collectively be referred to as "non-human animals".

Non-human large mammals subjected to the present invention may typically be domestic animals. The term "large" is used with intention to exclude small-sized mammals; and mammals that may be classified as middle-sized animals on detailed classification are also included in the non-human large mammals referred to in the present invention. Specific examples of the non-human large mammal include, but are not limited to, various ungulate animals including even-toed ungulates such as cattle, pigs, sheep, goats, wild boars, deer, camels, and hippopotamuses and odd-toed ungulates such as horses, rhinoceroses, and tapirs; and non-rodents excluding rabbits such as monkeys and dogs which are in general classified as large animals in classification of experimental animals; with cattle being particularly preferred.

Fish subjected to the present invention may typically be farmed fish. Farming techniques have recently been developed for various kinds of edible fish. Specific examples of the fish subjected to the present invention include, but are not limited to, tuna, yellowtail, mackerel, bonito, and horse mackerel.

In the present invention, a pluripotent cell(s) is(are) transplanted (injected) into an embryo at the cleavage stage that has a genome in which a function of nanos3 gene is inhibited, which embryo is derived from a non-human animal and which pluripotent cell(s) is(are) derived from another non-human animal. In animal individuals in which the function of the nanos3 gene is inhibited via knockout or the like, germ cells (gametes, namely sperm and eggs) are not formed. Therefore, transplantation of a pluripotent cell(s) in which nanos3 gene functions normally into an embryo in which a function of nanos3 gene is inhibited, which embryo is derived from a non-human animal and which pluripotent cell(s) is(are) derived from another non-human animal individual, results in complementation of the germ cells with the transplanted pluripotent cell(s), thereby making it possible to obtain animal individuals that produce germ cells originating in such another individual.

In the present invention, a non-human animal (a non-human large mammal or fish) to which inhibition of a function of nanos3 gene is applied is, for convenience, referred to as "the first non-human animal", and a non-human animal from which the pluripotent cell(s) for complementing germ cells is derived is, for the purpose of distinguishing it from the first one, referred to as "the second non-human animal". The first non-human animal and the second non-human animal may be animal individuals belonging to the same species or the same breed/strain (for example, cattle individuals, the Japanese Black individuals, and the like) or may be animals of different species or different breeds/strains (for example, sheep and cattle, Japanese Black and Holstein, and the like).

In the present invention, the phrase "to inhibit a/the function of a gene" refers to a decrease in or a loss/lack of production or accumulation of mRNA or protein that is originally encoded by a gene, which decrease or loss/lack is caused by, e.g., modifying at least part of a region where such a gene is present on a genome, or the like; and covers from a decrease in the function of a gene to a complete loss of the function. Gene modification methods for inhibiting the function of a particular gene are widely known in the art; and those skilled in the art can select and carry out them as appropriate. The methods are roughly divided into: gene disruption methods (knockout methods) whereby the function of a gene is deleted and gene knockdown methods whereby the function of a gene is decreased; and specific examples of the knockdown method include antisense methods and RNAi.

The inhibition of the function of nanos3 gene in the present invention is preferably loss-of-function caused by disruption (knockout) of the nanos3 gene. For example, the nanos3 gene can be knocked out by, in both alleles in a genome, deleting the coding region of nanos3 gene or a promoter region thereof or introducing mutation such as substitution or insertion to disable production of a normal nanos3 protein. For the sake of convenience in screening of a knockout cell line, all or part of the coding region of the nanos3 gene may be replaced by a marker gene sequence for drug resistance, fluorescent protein or the like.

One specific example of the gene knockout technique is a knockout method by homologous recombination using a targeting vector described in the Examples below. Other examples of the gene knockout methods include a zinc finger nuclease (ZFN) method (Porteus, M. H. et al. Gene targeting using zinc finger nucleases. Nat. Biotechnol. 23, 967-973 (2005).), a TALEN method (Christian, M. et al. Targeting DNA double-strand breaks with TAL effector nucleases. Genetics 186, 757-761 (2010).), and a CRISPR/Cas9 method (Sander, J. D. et al. CRISPR-Cas systems for editing, regulating and targeting genomes. Nat Biotechnol 32, 347-355 (2014).). An appropriate knockout method may be selected depending on the kind of non-human animals used for the gene knockout. In methods using a targeting vector, for example, the step of reconstructing an embryo by somatic cell nuclear transfer is required as described later; and in cases where the gene knockout is wished to be carried out in animals in which the efficiency of somatic cell nuclear transfer is low, such as pigs, or in animal species for which embryo reconstruction techniques by somatic cell nuclear transfer have not been established, the ZFN method, the TALEN method, and the CRISPR/Cas9 method, all of which do not require the step of somatic cell nuclear transfer, can be preferably employed.

In the knockout method using a targeting vector, genomic sequences upstream and downstream of a region that should be deleted may be amplified from the genomic DNA of an organism of interest by using PCR to prepare an upstream homology region and a downstream homology region; these homology regions and a marker gene may be then sequentially inserted into an appropriate plasmid vector to construct a targeting vector comprising a DNA construct for gene disruption in which the upstream homology region, the marker gene, and the downstream homology region are arranged in the order mentioned; and thereafter, this vector may be introduced into somatic cells (fibroblasts and the like) derived from the organism of interest by using a conventional method such as electroporation. Introduction of such a targeting vector to cells allows the construct for gene disruption to be introduced to an intended position on the genome via homologous recombination, thereby yielding a mutant allele where all or part of the nanos3 gene is replaced by the marker gene.

The size of the upstream homology region and the downstream homology region affect the efficiency of homologous recombination, and large-sized homology regions are used for biological species in which the efficiency is low. In gene disruption in mammals, the homology regions commonly used are about several kilobases in size. Although it is common that one homology region is about 1 to 3 kb in size (short arm) whereas the other homology region is about 5 kb or more (long arm), both homology regions may be prepared to have a size of about 5 kb. The base sequences shown in SEQ ID NOs: 3 and 4 are the genomic regions upstream and downstream of bovine nanos3 gene, and these regions or partial regions thereof with an appropriate size can be used as the homology region when the bovine nanos3 gene is knocked out.

Nanos3 gene has thus far been cloned in various animals including invertebrates and vertebrates. In cases where animals in which the nanos3 gene has not yet been cloned are employed as the first non-human animal to which inhibition of the function of nanos3 gene is applied, search may be carried out against whole genome sequence information (e.g. shotgun sequences) using sequence information of the already-identified nanos3 gene, such as human or mouse nanos3 gene, to identify a putative nanos3 gene region, thereby obtaining genomic sequence information necessary for inhibiting the function of nanos3 gene, such as homology regions to be incorporated into a targeting vector.

In mammalian cells, the frequency of introduction of a construct for gene disruption into a genome via homologous recombination is very low when compared with the frequency of random introduction not via homologous recombination. Because of this, when the nanos3 gene is knocked out according to the present invention, it is preferred to use a positive selection marker that confers drug resistance and a negative selection marker that confers drug sensitivity in combination. That is, in the above-described construct for gene disruption, a positive selection marker may be used as a marker gene that is incorporated between the two homology regions, and a negative selection marker gene may be arranged outside of the two homology regions (on the 5'-side of the upstream homology region, or on the 3'-side of the downstream homology region). If the construct is introduced to the genome by homologous recombination, a region outside of the homology region in the construct is not introduced to the genome, and therefore the drug sensitivity is not conferred by the negative selection marker gene. On the other hand, when the construct is introduced into the genome not via homologous recombination, the negative selection marker gene is also introduced into the genome, and therefore the drug sensitivity is conferred to such a transformant cell. Thus, by introducing the construct for gene disruption into somatic cells derived from the first non-human animal and thereafter carrying out screening with positive and negative selection markers, cells in which the construct is introduced into an appropriate site by homologous recombination to disrupt the nanos3 gene can be selected in an efficient fashion.

Specific examples of the commonly-used marker gene include, but are not limited to, as for the positive selection marker, neomycin resistance gene, blasticidin resistance gene, and puromycin resistance gene; and as for the negative selection marker, thymidine kinase gene and Diphtheria toxin fragment A (DT-A). Each of the markers is used in combination with an appropriate promoter, and those skilled in the art can appropriately select it depending on the kind of marker genes.

After the selection with the markers, the disruption of the gene is checked by PCR or Southern blotting, and cells having an allele where the nanos3 gene is disrupted are obtained. Those skilled in the art can as appropriate design primers used for PCR and a probe used for Southern blotting depending on the structure of a DNA construct for gene disruption.

As described above, the frequency of homologous recombination is very low in mammalian cells. The homologous recombination is highly unlikely to take place in both alleles at the same time, and thus the knockout usually occurs heterozygously. In order to obtain homozygous knockout cells, the introduction of the construct for gene disruption and the screening, both of which are described above, may be carried out again using a cell line that has been confirmed to be a heterozygous knockout cell line. The homozygous knockout cell can be appropriately selected by using a DNA construct for gene disruption comprising a drug resistant positive selection marker in preparation of heterozygous knockout cells and using a DNA construct for gene disruption comprising another drug resistant positive selection marker, which is different from the former, in preparation of homozygous knockout cells.

It is to be noted that, in order to increase the efficiency of homologous recombination, BML gene knockdown treatment may be carried out in addition to the nanos3 gene knockout treatment. It has been reported that BLM gene knockdown treatment increases the efficiency of homologous recombination in human cells (So S et al. Genes to Cells 2006; 11(4):363-371.), and thus knockdown of the BML gene is also similarly effective for improving the efficiency of homologous recombination in non-human animals subjected to the present invention. Sequence information and the like of the BML gene are also known and nucleic acid reagents for knocking down the BML gene of various animal species are commercially available, and thus those skilled in the art can carry out BML gene knockdown treatment by using as appropriate such commercially available products.

Subsequently, an embryo is reconstructed by using a somatic cell nuclear transfer technique from a cell(s) in which the function of nanos3 gene is inhibited in the manner as described above. The somatic cell nuclear transfer technique has also been an established technique in large mammals (see Nature, 385, p. 810-813, 1997; Science, 282 (5396), p. 2095-2098, 1998; Science, 298, p. 1188-1190, 2000; Nature, 407, p. 86-90, 2000; Nat Biotechnol., 18, P. 1055-1059, 2000; Cloning Stem Cells 9, 571-580 (2007); and the like). Specifically, a reconstructed embryo (nuclear transfer embryo) that is derived from the first non-human large mammal and has a genome in which the function of nanos3 gene is inhibited can be obtained by preparing an in vivo matured oocyte or in vitro matured oocyte of a large mammal, enucleating the resulting ovum to obtain an enucleated egg, transplanting a cell in which nanos3 is inhibited into the enucleated egg, and fusing the cells by electrical stimulation or the like.

This reconstructed embryo is activated and cultured up to the cleavage stage, and injected with at least one pluripotent cell derived from the second non-human large mammal in which nanos3 gene is normal (i.e. its function is not inhibited) to prepare a chimeric embryo. As for the number of pluripotent cells injected, at least one cell may be required; and plurality of cells, for example, several to ten and several cells are usually injected.

A pluripotent cell derived from the second non-human animal is not particularly restricted as long as it has pluripotency. If the second non-human animal is any of animal species whose ES cell or iPS cell line has been established, the ES cell or iPS cell line can be used. In the case of animal species for which such a cell line has not been established, a blastomere(s) from a fertilized egg can, for example, be used.

The developmental stage of an embryo from the first non-human animal at the time of injection of a pluripotent cell(s) is not particularly restricted as long as it is the cleavage stage, and may be any stage from the two-cell stage to the blastocyst stage. The stage may, for example, be the 4-cell stage, the 8-cell stage, the 16-cell stage, the morula stage, or the blastocyst stage. In general, the injection is preferably carried out at the morula stage to the blastocyst stage.

In an individual obtained by allowing the above-described chimeric embryo to develop, germ cells (gametes, namely eggs or sperm) originating in the second non-human large mammal, which is a different individual, are produced. By transferring this chimeric embryo to a surrogate mother (surrogate parent) to produce an offspring, a non-human large mammal that produces such gametes originating in the different individual can be obtained. The surrogate mother into which the chimeric embryo is transferred is usually a female individual belonging to the same species as the first non-human large mammal. For example, in the case where the first non-human large mammal is sheep and the second non-human large mammal is cattle, the surrogate mother into which the chimeric embryo is transferred is usually a female sheep individual.

The ZFN method, the TALEN method, and the CRISPR/Cas9 method, which are gene knockout methods that can be used in addition to a method using a targeting vector, are all techniques using an artificial nuclease prepared by fusing, to a nuclease, a DNA recognition site designed so that a desired base sequence is specifically recognized thereby (a zinc finger domain in the ZFN method, a DNA-binding domain of a TAL effector derived from the plant pathogen *Xanthomonas* in the TALEN method, and a guide RNA comprising a sequence complementary to a DNA sequence that should be cut in the CRISPR/Cas9 method). When a pair of these artificial nucleases (designed for each of the plus strand and the minus strand) is introduced into a cell, a double-stranded DNA is cut at an intended site to cause substitution, deletion, and/or insertion of bases due to repair failure during the process of repairing by non-homologous end joining (NHEJ), which leads to disruption of a gene of interest. By introducing a DNA construct for gene disruption comprising two homology regions as described above and the artificial nuclease into a cell, the construct for gene disruption is inserted into a target site during the process of repairing by homology-directed repair (HDR), and thus a desired sequence such as a marker gene sequence can be inserted into the target site.

According to those techniques, an artificial nuclease designed so that the nanos3 gene is targeted thereby is introduced into a fertilized egg from the first non-human animal to disrupt the nanos3 gene, and a fertilized egg with homozygous disruption is produced, thereby obtaining a fertilized egg (embryo) having a genome in which the nanos3 gene is knocked out. Hence, according to those techniques, a somatic cell nuclear transfer manipulation does not need to be carried out. Accordingly, in the case of animal species in which the efficiency of somatic cell nuclear transfer is low, these techniques may more preferably be used than the gene knockout method using a targeting vector. These techniques can also be used preferably in production of fish in which the nanos3 gene is knocked out.

The subsequent steps are the same as the steps explained above in the technique using a targeting vector. That is, a pluripotent cell(s) derived from the second non-human animal may be transplanted into the fertilized egg (embryo) in which the nanos3 gene on the genome is homozygously disrupted that is obtained in the manner as described above, to prepare the chimeric embryo. By allowing this chimeric embryo to develop, a non-human animal individual that produces gametes originating in a different individual can be obtained. In the case of mammals, the chimeric embryo may be transferred into a surrogate mother (surrogate parent) to yield an offspring. Naturally, in the case of fish, this embryo transfer step is not necessary.

Descendants of the non-human animal that produces gametes originating in a different individual obtained by allowing the chimeric embryo to develop can be obtained from the female and the male of such a non-human animal by natural mating or by artificial insemination or in vitro fertilization. In the case of in vitro fertilization, although an in vitro fertilized egg is usually transferred into a female individual of the non-human animal that produces gametes originating in a different individual produced by the method of the present invention, the in vitro fertilized egg may be transferred into a non-human animal different from the above-mentioned animal (for example, an individual belonging to the same species as the second non-human animal).

According to the present invention, it is, for example, possible to allow domestic animals that can be raised at a low cost to produce sperm or eggs of domestic animals that have to be raised expensively. Specific examples include sheep and goats, which can be raised at a low cost because they are more robust and can survive on poor food as compared with cattle, and moreover, show good reproductive efficiency thanks to their precocity Therefore, by using sheep or goats as the first non-human animal and using cattle as the second non-human animal, sheep or goat that produce bovine gametes can be obtained, and thus it becomes possible to provide bovine sperm for artificial insemination and bovine fertilized eggs under low cost management. Similarly, by using horse mackerel or mackerel as the first non-human animal and using tuna as the second non-human animal, horse mackerel or mackerel that produce tuna gametes can be obtained, and thus it becomes possible to mass-produce juvenile tuna for tuna farming at a low cost.

According to the method of the present invention, it is further possible to make a certain non-human animal produce gametes having desired genetic characteristics that the second non-human animal different from the former certain non-human animal possesses. Once a phyletic line of a non-human animal producing such gametes has been established, non-human animal individuals having the desired genetic characteristics can be mass produced by mating the female and the male (natural mating, artificial insemination, or in vitro fertilization) without resorting to somatic cell cloning techniques.

The term "desired genetic characteristics" include both genetic characteristics that occurred naturally in the second non-human animal and artificial genetic modification. Examples of the former include a characteristic of having a very high breeding value (for example, very high gain ability). The artificial genetic modification may be, for example, inhibition of the function of a desired gene, typically knockout of a desired gene.

In cases where gametes of a non-human animal in which a desired gene has been knocked out are made to be produced by another non-human animal, it is only required that the desired gene be knocked out in a pluripotent cell derived from the second non-human animal to be used for production of a chimeric embryo. Such a pluripotent cell derived from the second non-human animal having a genome in which the desired gene is knocked out can be basically obtained by using appropriate cells derived from the second non-human animal in the same procedure as described in the knockout of the nanos3 gene. In cases where a knockout method using a targeting vector is employed, a blastomere of a reconstructed embryo in which the desired gene is homozygously knocked out can be used as such a pluripotent cell. In cases where a knockout method using an artificial nuclease is employed, a blastomere of a fertilized egg in which the desired gene is homozygously knocked out can be used as such a pluripotent cell.

By using the method of the present invention, eggs and sperm in which a desired gene is knocked out can be steadily produced by non-human animal individuals in which the said gene is not knocked out. Non-human animals in which a particular gene is knocked out can be steadily obtained by natural mating or by artificial insemination or in vitro fertilization between female and male non-human animals created according to the method of the present invention that produce gametes in which a desired gene has been knocked out. According to the present invention, steady supply of individuals in which a particular gene is knocked out becomes practicable even in large animals.

EXAMPLES

The present invention is described below more concretely by way of Examples. However, the present invention is not limited to the following Examples.

1. Object

By taking advantage of a somatic cell nuclear transfer cloning technique and a gene recombination technique, production of gene knockout (KO) individuals has become possible even in large and medium-sized domestic animals. These techniques are the most effective techniques in functional analysis of a particular gene that is necessary for genetic breeding of domestic animals. However, the efficiency of producing an individual by using a somatic cell nuclear transfer cloning technique is very low, and as it stands, steady production of a large number of KO individuals is not practicable under the present circumstances. It has recently been reported in mice that, when a hybrid embryo is prepared by combining a gene KO early embryo with a normal embryo, the hybrid embryo shows normal development and birth while compensating deficiencies (such as deficient cell differentiation and organ deficiency) caused by cells originating in the KO embryo (Kobayashi et al., Cell 142, 787-799 (2010)). It has also been reported in mice that KO of a gene associated with germ cell differentiation, nanos3, results in no formation of eggs and sperm (Tsuda et al., SCIENCE 301, 1239-1241 (2003)). In this study, we investigated whether an individual that generates only gene-KO eggs (or sperm) can be produced when an embryo in which the nanos3 gene is knocked out and an embryo in which a particular gene is knocked out are combined to prepare a complemented embryo by using the blastocyst complementation method shown above. If such a technique is demonstrated to work, it becomes possible to steadily produce only KO individuals by mating and artificial insemination (FIG. 1: outline of the technique).

2. Test Methods and Materials

A. Construction of Bovine Nanos3 Gene Genome DNA KO Vector

A KO vector for a gene associated with germ cell differentiation, nanos3 gene, was constructed based on information of genomic structure of bovine nanos3 gene disclosed in the NCBI database.

Figure 2:
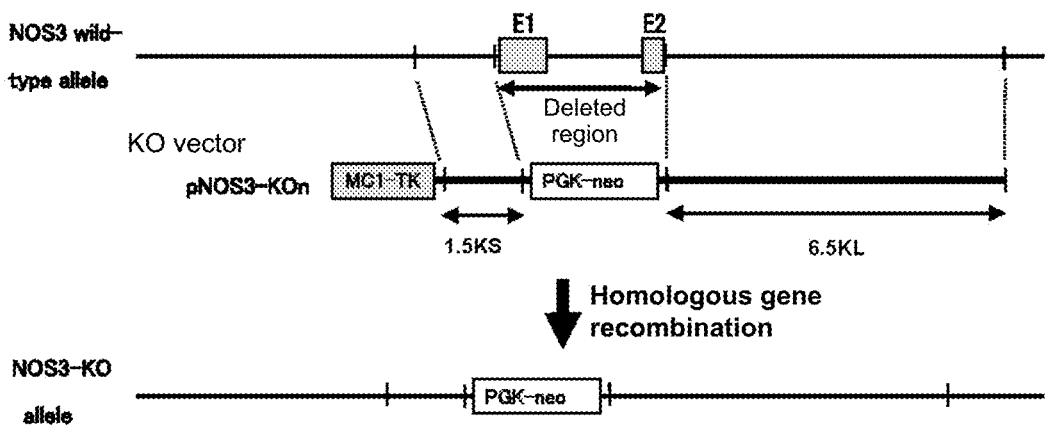
FIG. 2 shows the structure of the targeting vector for establishing a nanos3 heterozygous KO cell line and the structure of the allele where nanos3 is knocked out by such a vector.
Figure 3:
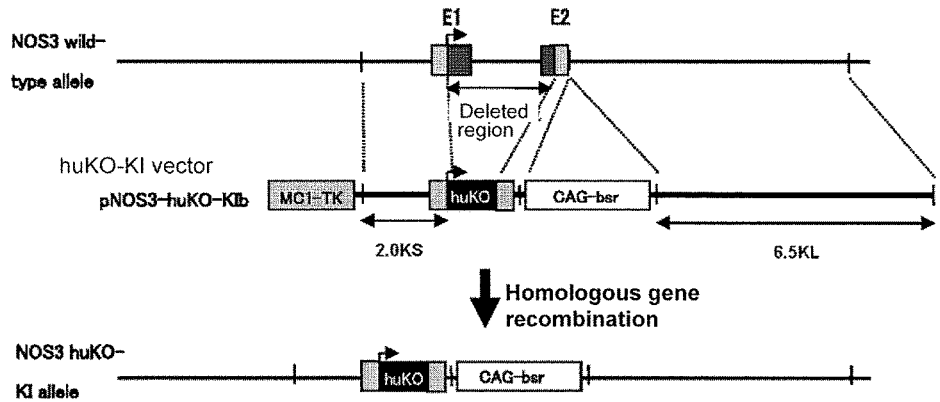
FIG. 3 shows the structure of the targeting vector for establishing a nanos3 homozygous KO cell line and the structure of the allele where nanos3 is knocked out by such a vector.

In order to construct a KO vector (pNOS3-KOn) for use in hetero KO manipulation, genomic regions flanking to the nanos3 gene (1.5 kb and 6.5 kb fragments: FIG. 2) were cloned by PCR cloning method. As a template DNA, genome DNA extracted from fibroblasts from a fetus of the Japanese Black was used. A sense primer: CTCTCCGTTG-CATCCATGCC (SEQ ID NO: 6) and an antisense primer: AGCCACTGACCTTCCAGCTGAC (SEQ ID NO: 7) were used for PCR amplification of the 1.5 kb fragment (1.5 kS) (a region from 333 nt to 1879 nt of SEQ ID NO: 3), which fragment was used as a short arm of the vector. On the other hand, a sense primer: GGACAAGGTATCGTGAACTGC (SEQ ID NO: 8) and an antisense primer: AACACGAG-GAGCACCTTCTTGC (SEQ ID NO: 9) were used for amplification of the 6.5 kb fragment (6.5 kbL) (a region from 283 nt to 6809 nt of SEQ ID NO: 4), which fragment was used as a long arm of the vector. The pNOS3-KOn vector was constructed by inserting a selection marker PGK-neo unit (a neomycin resistance gene with a PGK promoter) so that the entire nanos3 gene (exons 1 and 2) would be deleted. The pNOS3-KOn vector was constructed in the form where the short arm 1.5 kS and the long arm 6.5 kL were located in the 5' side and the 3' side of the PGK-neo unit, respectively, and a genetic marker for negative selection MC1-TK (a herpes thymidine kinase gene with an MC1 promoter) was further located in the 5' side of 1.5 kS (FIG. 2).

A huKO-knock in (KI) vector (pNOS3-huKO-KIb) was constructed as a vector for use in homozygous KO manipulation, the vector having a structure in which part of a protein coding region of the nanos3 gene was replaced by cDNA encoding a fluorescent protein, Kusabira-Orange (huKO) (FIG. 2). A cDNA fragment of Kusabira-Orange was synthesized by Eurofins Genomics K. K. by contract and used for vector construction. The sequence of the short arm comprising cDNA of huKO (3.0 kb sequence composed of 2.0 k bovine genome sequence+0.66 k huKO+0.35 k bovine genome sequence) is shown in SEQ ID NO: 5. In SEQ ID NO: 5, the sequence from 2049 nt to 2709 nt is the cDNA sequence of huKO. As for a selection marker, a CAG-bsr unit (a blasticidin S resistance gene with a CAG promoter) was used (FIG. 2).

B. Introduction of KO Vector into Fibroblasts Derived from Bovine Fetus, Selection Culturing, and Establishment of KO Cell Line Introduction of the pNOS3-KOn vector to fibroblasts (#906 female cell line) derived from a bovine (the Japanese Black) fetus, selection culturing, and establishment of a KO cell line were carried out according to methods previously reported (Sendai, Study Reports of Central Institute for Feed and Livestock, 1501-622 (2009); and Sendai, Y. et al., Transplantation 81, 706-766 (2006)). In addition, because it had been reported that the efficiency of homologous recombination was increased by knocking down the BLM gene in human cells (So S et al. Genes to Cells 2006; 11(4):363-371.), bovine BML gene was also knocked down for the purpose of increasing the efficiency of homologous recombination in the nanos3 knocking out. Knocking down of bovine BML gene was carried out according to a method previously reported (Sendai, Study Reports of Central Institute for Feed and Livestock, 1501-604 (2009)) using stealth RNA for bovine BML (synthesis position 2656) which was prepared by Invitrogen by contract. In the establishment of the homozygous KO cell line, pNOS3-huKO-KIb vector was introduced into a cell line (line #3933) derived from a nanos3 heterozygous KO fetus, and the resulting cells were cultured in a medium containing two kinds of selection agents (neomycin: G418 and blasticidin S).

PCR analysis for confirming KO was carried out according to a conventional method. The base sequences of primers used in the analysis are shown below.

```
P1:
                                      (SEQ ID NO: 10)
    AACACGGTGAAGCTCACTTAGG

P2:
                                      (SEQ ID NO: 11)
    CATGCTCCAGACTGCCTTGG

P3:
                                      (SEQ ID NO: 12)
    CTCTCCGTTGCATCCATGCC

P4:
                                      (SEQ ID NO: 13)
    CTTCATCTCGGGCTTGATCGTCG
```

-continued

P5:
(SEQ ID NO: 14)
GCTTCATCCTTGAGCACGTGG

P6:
(SEQ ID NO: 15)
CCACGTGCTCAAGGATGAAGC

P7:
(SEQ ID NO: 16)
CTGATACGTAAGCCTAGCTACTCG

Figure 4:
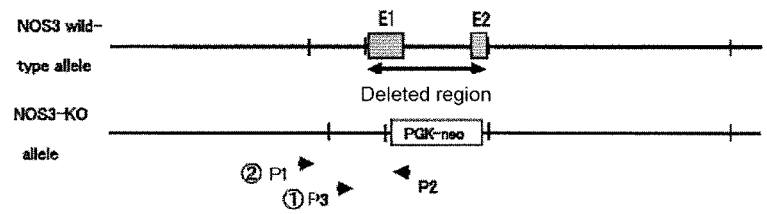
FIG. 4 shows illustration of PCR analysis for confirming nanos3 heterozygous KO and the results of the analysis.
Figure 4:
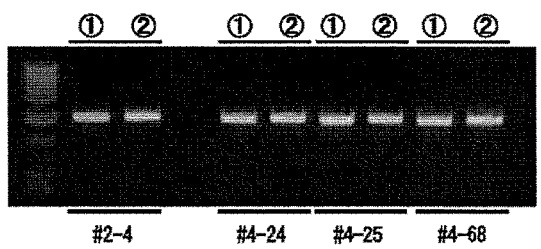
Figure 4:
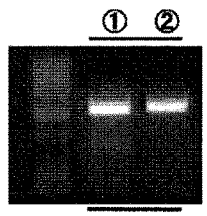
Figure 5:
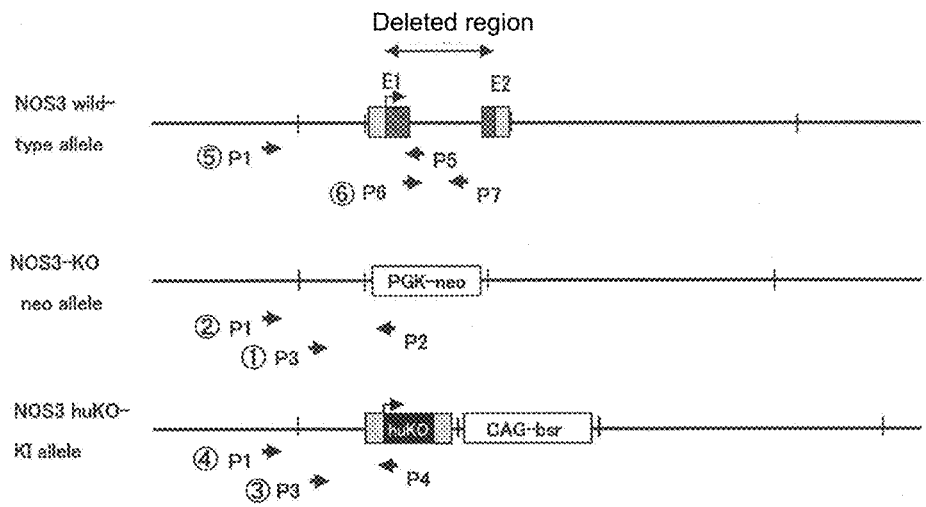
FIG. 5 shows illustration of PCR analysis for confirming nanos3 homozygous KO and the results of the analysis.
Figure 5:
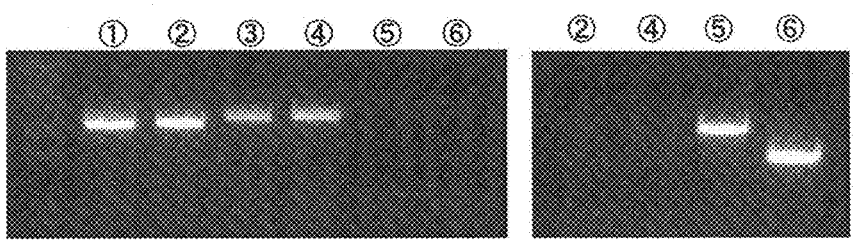
Figure 5:
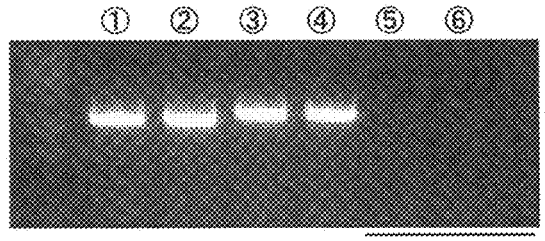

FIG. 4 and FIG. 5 show the region for which each of the primers was designed. For confirmation of heterozygous KO, P3-P2 (to amplify part of the construct within the vector for heterozygous KO) and P1-P2 (to detect an allele where the construct for heterozygous KO was inserted at a correct position) were used (FIG. 4). For confirmation of homozygous KO, in addition to P3-P2 and P1-P2, P3-P4 (to amplify part of the construct within the vector for homozygous KO), P1-P4 (to detect an allele where the construct for homozygous KO was inserted at a correct position, P1-P5 (to detect wt allele), and P6-P7 (to detect wt allele) were used.

C. Somatic Cell Nuclear Transfer and Collection of Fetus

Using a cell line in which heterozygous KO or homozygous KO of the nanos3 gene had been confirmed by the PCR analysis as a nuclear donor, somatic cell nuclear transfer procedures were carried out according to a previous report (Ideta, A. et al. Cloning Stem Cells 9, 571-580 (2007)) to prepare a nuclear transfer embryo (reconstructed embryo). Briefly, the procedure is described as follows.

A follicular ova were collected by aspiration from bovine ovary from a slaughterhouse and subjected to maturation culture for about 20 hours. Cumulus cells were removed by using hyaluronidase (Sigma) and then eggs in which extrusion of the first polar body was confirmed were picked out. A nuclear donor was inserted into the perivitelline space of an enucleated recipient egg and the cells were fused by electrical stimulation. The resultant was artificially activated by using calcium ionophore (Sigma) or the like for the purpose of promoting development of a reconstructed embryo. Subsequently, the resultant was cultured in vitro in a culture medium for development, and the development was monitored.

The nuclear transfer embryo was implanted into a bovine recipient. A fetus at about 200 days of gestation was taken out by caesarean section and the ovary of the fetus was observed. Tissue of the ovary was fixed with a 10% neutral buffered formalin solution and subjected to a paraffin embedding procedure to prepare tissue sections. The sections were stained with hematoxylin-eosin (HE), and the tissue was observed in optical microscopy.

D. Complementation of Germ Cells in Nanos3-KO Cattle

Blastomeres (7 to 10 blastomeres) of Holstein embryo that had been fertilized in vitro were injected into a nanos3-KO nuclear transfer embryo (morula), and the resultant was cultured in vitro for two days. The grown chimeric embryo was implanted into a bovine recipient. A fetus at about 140 days of gestation was taken out by caesarean section, and the ovary of the fetus was observed. In addition, a chimeric rate (the content of Holstein cells) of each organ of the chimeric fetus was examined by using a real time PCR method.

3. Results and Discussion (1) Cloning of Bovine Nanos3 Gene Genome and Construction of Gene KO Vector It has been reported that, in an experiment to produce a KO individual using mice, when a gene associated with germ cell differentiation, nanos3, is knocked out, division potential of primordial germ cells present at an early developmental stage decreases and migration into the genital ridge does not take place, resulting in no formation of eggs and sperm in the ovary and the testis of born KO individuals (Tsuda et al., SCIENCE 301, 1239-1241 (2003)). In addition, recent studies have showed that, in mice and pigs, when an early embryo which has become incapable of forming an organ or the like because of KO of a particular gene is combined with an undifferentiated cell derived from a normal early embryo, the cell derived from the normal embryo complements the KO deficient cell in the developing hybrid embryo (blastocyst complementation), resulting in formation of a normal organ (Kobayashi et al., Cell 142, 787-799 (2010) and Matsunari et al., PNAS 110(12), 4557-4562 (2013)). These results suggest that when an embryo in which nanos3 gene is knocked out is combined with an embryo in which a particular gene is knocked out to prepare a hybrid complemented embryo, an individual that generates only eggs (or sperm) in which the particular gene is knocked out may be produced, and also suggest that a system for steadily producing individuals in which the particular gene is knocked out may be realized (FIG. 1). In the present study, in order to confirm this hypothesis, an attempt was made to establish a KO cell line with the aim of producing a bovine nanos3 gene KO individual.

Bovine nanos3 gene was deduced (XM_002688743, SEQ ID NO: 1) from genomic information. We deduced bovine exons by comparing sequence information deposited under XM_002688743 with exon information of human nanos3 gene to find two putative exons. The sequences of these putative exons (1 and 2) were analyzed by using NCBI BLAST, and as a result, the chromosome (chromosome 7) on which each of the bovine nanos3 exons was located and a flanking gene sequence thereof (NC007305.5, region 10061880) were acquired. From the above results, the presence of nanos3 gene in cattle was confirmed, and it was revealed that, similarly to the murine gene, the gene was constituted by two exons (FIG. 2). Genomic regions flanking to the nanos3 gene (1.5 kb and 6.5 kb fragments: FIG. 2) for constructing a nanos3 gene KO vector were cloned by using a PCR cloning method.

Because the nanos3 gene is not expressed in fibroblasts, a positive-negative selection type was adopted as the KO vector, and the vector was constructed so that the entire nanos3 gene was deleted (FIG. 2). PGK-neo was used as a drug resistance gene for positive selection. MC1-TK was used as a drug susceptibility gene for negative selection (FIG. 2: pNOS-KOn). In order to establish a homozygous KO cell line, a KO-huKO-KI vector was constructed, in which vector part of the protein coding region of the nanos3 gene was replaced by cDNA encoding a fluorescent protein, Kusabira-Orange (huKO). CAG-bsr was used as a drug resistance gene for selection (FIG. 2: pNOS-huKO-KIb). When a nuclear transfer animal is produced using a NOS3-KO-KI cell line established with this vector as a donor, the location where germ-line cells (such as primordial germ cells) expressing the nanos3 gene are present can be visualized thanks to huKO fluorescence (FIG. 2: pNOS-huKO-KIb).

(2) Establishment of Bovine Nanos3 Gene KO Cell Line

Using the constructed KO vector (pNOS3-KOn), fibroblasts derived from a female fetus of the Japanese Black (line #906 (female)) was subjected to KO manipulation, and a heterozygous KO cell line was first established. An experiment for establishing the KO cell line was carried out four times, and nine wells out of 411 wells tested were judged to be knocked out (Table 1). It was suggested from a detailed PCR analysis that cells which were derived from a single colony and in which a homologous recombination reaction took place at the correct position were proliferating in each of the four wells out of those nine wells that were judged to be knocked out (lines #2-4, #4-24, #4-25, #4-68) (FIG. 4). Of these four lines, #4-68 which exhibited better cell proliferative properties was employed to produce and collect a nuclear transfer clone fetus and to establish a cell line. As a result, one fetus was successfully produced and collected, and a cell line derived from the fetus was also successfully established (line #3933). The heterozygous KO could also be confirmed from a genomic PCR analysis (FIG. 4).

TABLE 1

Establishment of bovine nanos3 heterozygous KO cell lines

| | G418/GCV resistant well | KO well |
|---|---|---|
| Experiment 1 | 111 | 0 |
| Experiment 2 | 81 | 2 (#2-4) |
| Experiment 3 | 78 | 1 |
| Experiment 4 | 141 | 6 (#4-24, #4-25, #4-68) |
| | 411 | 9 |

Cell line: 906 (♂) (nanos3 wt/wt)
The number of cells: 5 × 10$^6$ (BLM-RNAi treatment: cultured for 24 hr)
Introduction: TV 5 μg, Electroporation (220 V, 950 μF), seeded into four 6-well plates.

Subsequently, we tried to establish a homozygous KO cell line by introducing the KO-huKO-KI vector (pNOS3-huKO-KIb) into the established heterozygous KO cells (line #3933). An experiment for the establishment was carried out twice, and as a result, 15 wells out of 221 wells tested were judged to be homozygous KO-huKO-KI (Table 2). It was suggested from a detailed PCR analysis that one well out of these 15 wells that were judged to be homozygous KO-huKO-KI contained cells that were derived from a single colony and exhibited proliferative properties and in which a homologous recombination reaction took place at a correct position (line #2-36) (FIG. 5). These cells were employed to produce and collect a nuclear transfer fetus and to establish a cell line. As a result, one fetus was successfully produced and collected, and a cell line derived from the fetus could be established (line #Y6158). The homozygous KO could also be confirmed from a genomic PCR analysis (FIG. 5).

TABLE 2

Establishment of bovine nanos3 homozygous KO cell lines

| | G418 + Blast/GCV resistant well | KO-KI well |
|---|---|---|
| Experiment 1 | 110 | 12 |
| Experiment 2 | 111 | 3 (#2-36) |
| | 221 | 15 |

Cell line: nanos3 heterozygous KO fetal cell line (#3933; nanos3 —/wt)
The number of cells: 5 × 10$^6$ (BLM-RNAi treatment: cultured for 24 hr)
Introduction: TV 5 μg, Electroporation (220 V, 950 μF), seeded into four 6-well plates.

(3) Lack of Germ Cells in Nanos3 Homozygous KO Fetus

Figure 6:
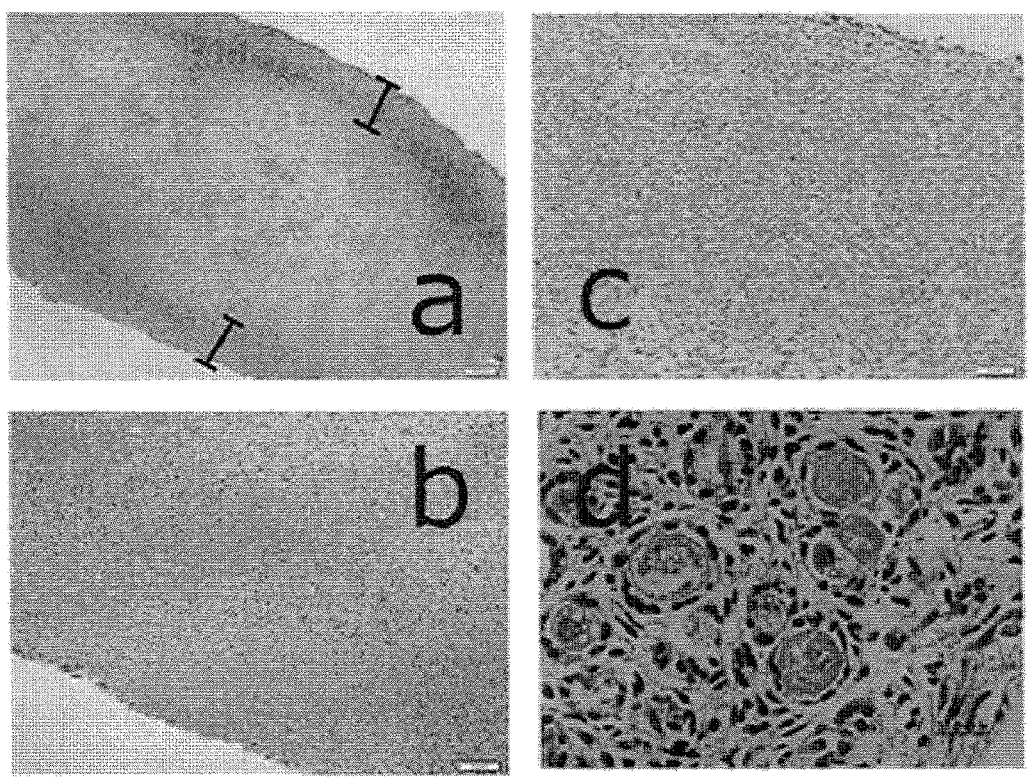
FIG. 6 shows the tissue images of the ovary of nanos3 homozygous KO fetus and non-KO fetus (about 200 days of gestation). Panel a: the ovary of the nanos3 homozygous KO fetus (low magnification); panels b and c: higher magnification images of panel a; and panel d: the ovary of the non-KO fetus which serves as a control. In panel d, primary follicles are observed, but not in panels a to c.

Tissue images of the ovary of the nanos3 homozygous KO fetus are shown in FIG. 6. In an approximately age-matched non-KO fetus, a large number of primary follicles are observed in the ovarian cortex and germ cells are normally formed (FIG. 6 *d*), whereas, no follicular cells were observed in the ovary of the nanos3 homozygous KO fetus (FIG. 6 *a* to *c*). Thus, it was revealed that primordial germ cells of the nanos3 KO cattle died by apoptosis at an early embryonic stage and the organism (194 days of gestation) completely lacked germ cells.

(4) Complementation of Germ Cells in Nanos3 Homozygous KO Cattle

Figure 7:
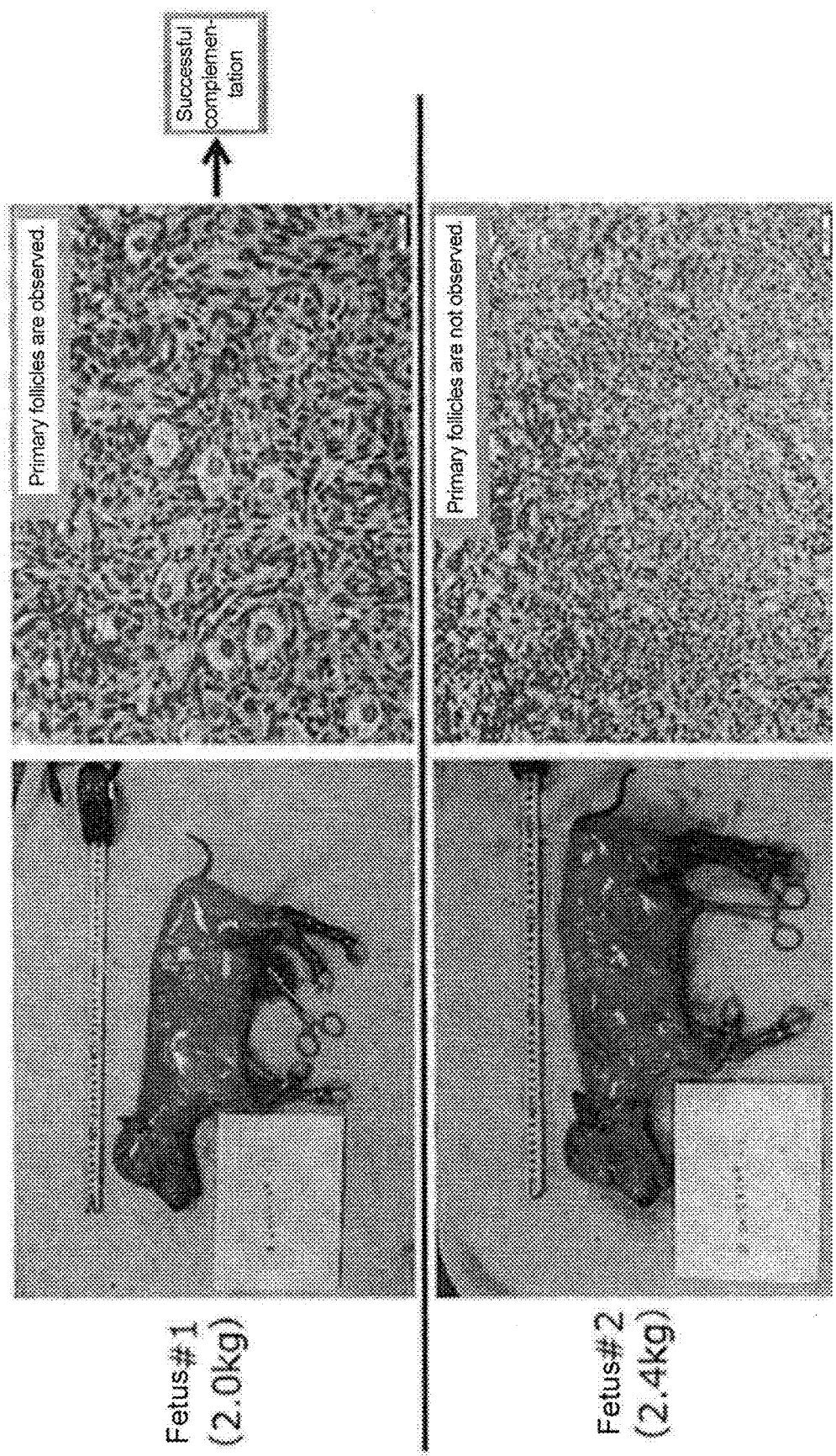
FIG. 7 shows the tissue images of the ovary of two fetal individuals (141 days of gestation) derived from the chimeric embryo that was produced by injecting blastomeres of Holstein embryo fertilized in vitro into the nanos3 homozygous KO nuclear transfer embryo (morula).

FIG. 7 shows tissue images of the ovary of the fetus (141 days of gestation) that developed from the chimeric embryo produced by injecting blastomeres (7 to 10 blastomeres) of Holstein embryo that had been fertilized in vitro into the nanos3-KO nuclear transfer embryo (morula). In one of two chimeric fetuses, primary follicles could be observed in the ovary. Thus, it was revealed that the ovary of the nanos3-KO cattle was complemented with the germ cells derived from the donor cells by the blastocyst complementation method.

A chimeric rate (the content of Holstein cells) of each organ of the chimeric fetus was examined by real time PCR, and as a result, the following rates were found: the brain, 12.1%; the heart, 20.2%; the liver, 1.8%; the uterus, 22.4%; and the ovary, 15.8%. It follows that the bovine fetus produced here is a chimeric individual between the Japanese Black and Holstein, and Holstein's germ cells are formed in the ovary.

The invention claimed is:

1. A method for producing a non-human large mammal or fish that produces gametes originating in a second non-human large mammal or fish, said method comprising
transplanting at least one blastomere derived from the second non-human large mammal or fish as a donor cell into an embryo derived from a first non-human large mammal or fish, said embryo being at a cleavage stage and having a genome in which a function of nanos3 gene is inhibited, to prepare a chimeric embryo between the first non-human large mammal and the second non-human large mammal or between the first fish and the second fish, and
allowing said chimeric embryo to develop into an individual,
wherein in the transplanting step, no other donor cells than said at least one blastomere are transplanted into said embryo.

2. The method according to claim 1, wherein inhibition of a function of nanos3 gene is carried out by knocking out said nanos3 gene by homologous recombination.

3. The method according to claim 2, wherein the knocking out of said nanos3 gene by homologous recombination uses at least one positive selection marker for drug resistance and at least one negative selection marker for drug sensitivity.

4. The method according to claim 3, wherein the at least one positive selection marker is selected from the group consisting of neomycin resistance gene, blasticidin resistance gene, and puromycin resistance gene.

5. The method according to claim 3, wherein the at least one negative selection marker is selected from the group consisting of thymidine kinase gene and diphtheria toxin fragment A (DT-A).

6. The method according to claim 3, wherein 7 to 10 blastomeres derived from the second non-human large mammal or fish as a donor cell are transplanted into an embryo derived from a first non-human large mammal or fish.

7. The method according to claim 6, wherein both of said first non-human large mammal and said second non-human large mammal are cattle.

8. The method according to claim 7, where the cattle is a Japanese Black or a Holstein.

9. The method according to claim 1 or 2, said cleavage stage is a morula stage or blastocyst stage.

10. The method according to claim 1, wherein the method produces a non-human large mammal or fish that produces gametes that originate in the second non-human large mammal or fish blastomere and have a genetic characteristic which the second non-human large mammal or fish has.

11. The method according to claim 10, wherein said genetic characteristic is artificial genetic modification.

12. The method according to claim 11, said artificial genetic modification is gene knockout.

13. The method according to claim 1, wherein said method is a method of producing a non-human large mammal that produces gametes that originate in the second non-human large mammal or fish, said method further comprising transferring said chimeric embryo into a non-human surrogate mother to obtain an offspring.

14. The method according to claim 13, wherein at least one of said first non-human large mammal and said second non-human large mammal is cattle.

15. A method for producing an egg of a non-human large mammal or fish, said method comprising collecting an egg from a female individual of said non-human large mammal or fish produced by the method according to claim 1.

16. A method for producing sperm of a non-human large mammal or fish, said method comprising collecting sperm from a male individual of said non-human large mammal or fish produced by the method according to claim 1.

17. A method for producing a fertilized egg of a non-human large mammal or fish, said method comprising fertilizing an egg collected from a female individual with sperm collected from a male individual to obtain a fertilized egg, wherein the female and male individual each is the non-human large mammal or fish produced by the method according to claim 1.

18. A method for producing a non-human large mammal or fish, said method comprising obtaining a descendant of female and male non-human large animals or fish produced by the method according to claim 1 by natural mating, artificial insemination, or in vitro fertilization.

19. A method for producing a bovine that produces gametes originating in a second bovine, said method comprising:

transplanting at least 7 to 10 blastomeres derived from a Japanese Black bovine into an embryo derived from Holstein bovine, said embryo being at a cleavage stage and having a genome in which a function of nanos3 gene is inhibited, to prepare a chimeric embryo between the Japanese Black bovine and the Holstein bovine, and allowing said chimeric embryo to develop into an individual, wherein in the transplanting step, no other donor cells than said 7 to 10 blastomeres are transplanted into said embryo.

* * * * *